(12) United States Patent
Katsuragi

(10) Patent No.: US 10,316,205 B2
(45) Date of Patent: Jun. 11, 2019

(54) RECORDED MATTER, INK FOR RECORDED MATTER, AND INK

(71) Applicant: Koji Katsuragi, Kanagawa (JP)

(72) Inventor: Koji Katsuragi, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 8 days.

(21) Appl. No.: 15/716,682

(22) Filed: Sep. 27, 2017

(65) Prior Publication Data

US 2018/0094150 A1     Apr. 5, 2018

(30) Foreign Application Priority Data

Sep. 30, 2016   (JP) ................................ 2016-194453
Aug. 22, 2017   (JP) ................................ 2017-159390

(51) Int. Cl.
*C09D 11/40*     (2014.01)
*C09D 11/107*    (2014.01)
(Continued)

(52) U.S. Cl.
CPC .......... *C09D 11/107* (2013.01); *C08F 220/18* (2013.01); *C08L 25/14* (2013.01);
(Continued)

(58) Field of Classification Search
None
See application file for complete search history.

(56) References Cited

U.S. PATENT DOCUMENTS

2008/0044582 A1* 2/2008 Kitagawa ............. D06P 1/5221
                                                427/412
2010/0028964 A1* 2/2010 Hama ................... C11B 9/0053
                                                435/155
(Continued)

FOREIGN PATENT DOCUMENTS

JP    2003-313481    11/2003
JP    2014-028964    2/2014

*Primary Examiner* — Erica S Lin

(74) *Attorney, Agent, or Firm* — Oblon, McClelland, Maier & Neustadt, L.L.P.

(57) ABSTRACT

Recorded matter includes a recording medium and an image on the recording medium. The image comprises a hollow resin including a copolymer of the structure unit represented by the following chemical formula 1 and the structure unit represented by the following chemical formula 2. Also, in an IR spectrum of the image, the image satisfies the following ratio: $3.0 \leq Y/X \leq 6.0$, where X represents the absorbance of the image at the maximum absorption wavelength in a range of from 1,590 to 1,610 $cm^{-1}$ and Y represents the absorbance of the image at the maximum absorption wavelength in a range of from 1,720 to 1,740 $cm^{-1}$.

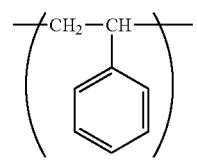

Chemical formula 1

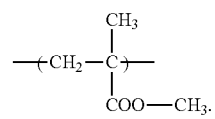

Chemical formula 2

10 Claims, 1 Drawing Sheet

(51) Int. Cl.

| | |
|---|---|
| *C09D 11/102* | (2014.01) |
| *C08F 220/18* | (2006.01) |
| *C08L 25/14* | (2006.01) |
| *C09D 11/106* | (2014.01) |
| *C09D 11/32* | (2014.01) |
| *C09J 133/12* | (2006.01) |
| *C08L 75/04* | (2006.01) |
| *C08L 33/12* | (2006.01) |
| *G01N 21/35* | (2014.01) |
| *C08L 83/04* | (2006.01) |

(52) U.S. Cl.
CPC .......... *C09D 11/102* (2013.01); *C09D 11/106* (2013.01); *C09D 11/32* (2013.01); *C09J 133/12* (2013.01); *C08L 33/12* (2013.01); *C08L 75/04* (2013.01); *C08L 83/04* (2013.01); *C08L 2205/20* (2013.01); *G01N 2021/3595* (2013.01)

(56) References Cited

U.S. PATENT DOCUMENTS

| | | | | |
|---|---|---|---|---|
| 2011/0318510 | A1* | 12/2011 | Seguchi | B41M 5/506 |
| | | | | 428/32.33 |
| 2013/0052434 | A1* | 2/2013 | Asahi | G02B 1/105 |
| | | | | 428/212 |
| 2015/0258833 | A1 | 9/2015 | Katsuragi | |
| 2016/0177116 | A1 | 6/2016 | Katsuragi et al. | |

* cited by examiner

RECORDED MATTER, INK FOR RECORDED MATTER, AND INK

CROSS-REFERENCE TO RELATED APPLICATIONS

This patent application is based on and claims priority pursuant to 35 U.S.C. § 119 to Japanese Patent Application Nos. 2016-194453 and 2017-159390, filed on Sep. 30, 2016 and Aug. 22, 2017, respectively, in the Japan Patent Office, the entire disclosures of which are hereby incorporated by reference herein.

BACKGROUND

Technical Field

The present disclosure relates to recorded matter, an ink for the recorded matter, and an ink.

Description of the Related Art

In general, titanium dioxide is used as a coloring material or white ink in inkjet methods.

In addition, ink is known which uses coloring material including a hollow resin particle with a hollow inside.

Such a hollow resin particle demonstrates whiteness utilizing the difference of refractive index between the hollow inside and the outer crust of the hollow resin particle. For example, an ink composition including a hollow resin particle and an anti-transparency agent of the hollow resin particle has been proposed.

Also, ink including hollow resin particles having different particle diameters by at least 0.1 μm has been proposed.

SUMMARY

According to an embodiment of the present invention, provided is an improved recorded matter including a recording medium and an image on the recording medium. The image includes a hollow resin including a copolymer of the structure unit represented by the following chemical formula 1 and the structure unit represented by the following chemical formula 2. Also, in an IR spectrum of the image, the image satisfies the following ratio: $3.0 \leq Y/X \leq 6.0$, where X represents the absorbance of the image at the maximum absorption wavelength in a range of from 1,590 to 1,610 $cm^{-1}$ and Y represents the absorbance of the image at the maximum absorption wavelength in a range of from 1,720 to 1,740 $cm^{-1}$.

BRIEF DESCRIPTION OF THE SEVERAL VIEWS OF THE DRAWINGS

Various other objects, features and attendant advantages of the present invention will be more fully appreciated as the same becomes better understood from the detailed description when considered in connection with the accompanying drawings in which like reference characters designate like corresponding parts throughout and wherein.

DETAILED DESCRIPTION OF THE EMBODIMENTS

Figure 1:
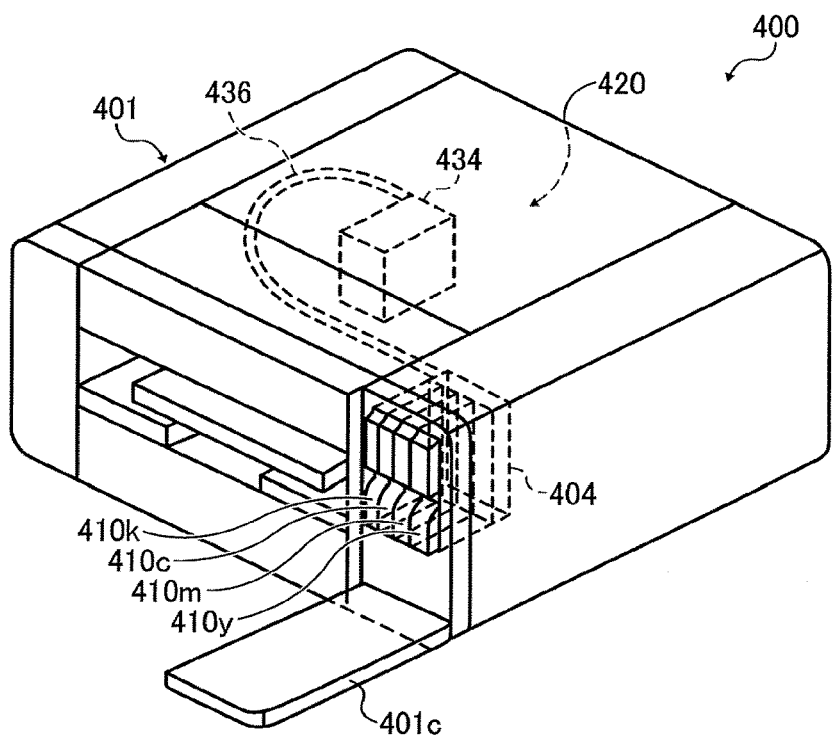
FIG. 1 is a diagram illustrating a perspective view of an example of an inkjet recording device.

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

As used herein, the singular forms "a", "an", and "the" are intended to include the plural forms as well, unless the context clearly indicates otherwise.

Moreover, image forming, recording, printing, modeling, etc. in the present disclosure represent the same meaning, unless otherwise specified.

Recorded Matter

The recorded matter of the present disclosure includes a recording medium and an image on the recording medium. The image contains a hollow resin containing a copolymer of the structure unit represented by the following chemical formula 1 and the structure unit represented by the following chemical formula 2. The image satisfies the following ration: $3.0 \leq Y/X \leq 6.0$. X represents an absorbance of the image at the maximum absorption wavelength in a range of from 1,590 to 1,610 $cm^{-1}$ and Y represents an absorbance of the image at the maximum absorption wavelength in a range of from 1,720 to 1,740 $cm^{-1}$. When the ratio (Y/X) is from 3.0 to 6.0, good luminosity is obtained even when the image is heated.

When the ratio (Y/X) is from 3.0 to 6.0 and the change ratio of the luminosity is 25 percent or less before and after the image is heated at 110 degrees C. for 60 seconds, whiteness of the recorded matter can be preferably maintained even when the recorded matter is stored for a long period of time.

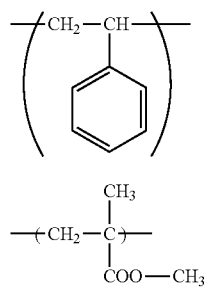

Chemical formula 1

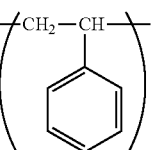

Chemical Formula 1

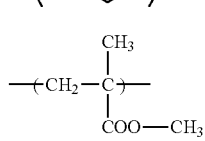

Chemical formula 2

Chemical Formula 2

The recorded matter of the present disclosure is made based on the knowledge about typical technology that when a hollow resin particle contacts an organic solvent having an SP value close to that of the outer crust resin of the hollow resin particle, the outer crust resin is dissolved, which leads to occurrence of crushing of the hollow resin particle (causing decrease of luminosity L*).

The recorded matter of the present disclosure includes a recording medium and an image formed thereon. Also, the recorded matter may have an under layer or top layer on or underneath the image. The under layer can be formed by, for example, applying a pre-processing fluid to the recording medium. The top layer can be formed by, for example, applying a post-processing fluid to the image.

Image

The image contains a hollow resin and preferably other resins. It may furthermore optionally contain other components.

The image can be formed by using ink.

Ratio (Y/X)

In an infrared spectroscopy (IR) spectrum of the image, the image satisfies the following ratio: $3.0 \leq Y/X \leq 6.0$, where X represents an absorbance of the image at the maximum absorption wavelength in a range of from 1,590 to 1,610 $cm^{-1}$ and Y represents an absorbance of the image at the maximum absorption wavelength in a range of from 1,720 to 1,740 $cm^{-1}$. When the ratio (Y/X) is 3.0 or greater, the strength of the hollow resin can be improved. As a consequence, it is possible to suppress degradation of luminosity occurring when the resin of the hollow resin is dissolved due to energy such as heat. The void (hollow) formed by the hollow resin can be maintained and decrease of luminosity can be suppressed after an image is formed. Conversely, when the ratio (Y/X) is 6.0 or less, luminosity of the image can be improved and sedimentation property of the hollow resin particle in the ink can be improved.

The absorbance can be measured by using, for example, microscopic FT-IR measuring device (iN10MX/iZ10, manufactured by Thermo Fisher Scientific K.K.) and analysis software (OMNIC). Also, the image portion (ink solid portion) can be optionally cut out from the recorded matter for measuring of IR spectrum.

Change Ratio of Luminosity

The change ratio of luminosity of the image before and after the image is heated at 110 degrees C. for 60 seconds is preferably 25 percent or less and more preferably 21 percent or less. When the change ratio is 25 percent or less, it is possible to obtain good luminosity even when the image is heated.

The change ratio can be suppressed to 25 percent or less because luminosity of the image and the strength of the hollow resin can be improved if the ratio (Y/X) is from 3.0 to 6.0. In the present disclosure, white has a luminosity (L*) of 20 or greater in a white image.

The change ratio of the luminosity can be calculated according to the following relation 1 using the initial value and the value obtained after the image is heated at 110 degrees C. for 60 seconds. The luminosity (L*) can be measured by using, for example, a spectrophotometer (product name: 939, manufactured by X-Rite).

The change ratio (percent)={(initial value−value obtained after heated at 110 degrees C. for 60 seconds)/initial value}×100      Relation 1

The image in the recorded matter includes a hollow resin so that the image can have voids (hollow) in the image in the recorded matter.

In the present disclosure, the hollow means a hollow portion formed in the image of the recorded matter.

The average diameter of the hollow in the image of the recorded matter has no particular limit and can be suitably selected to suit to a particular application. For example, it is preferably from 0.04 to 0.8 μm.

As the average diameter of the hollow in the image of the recorded matter, for example, it is possible to use the average of 10 hollows selected at random while observing the cross section of the recorded matter. If the hollow is not a true circle, the maximum of the diameter is used to calculate the average diameter.

An example of the microscope is JSM-6510 (manufactured by JEOL Ltd.).

Hollow Resin

The hollow resin contained in the image includes a copolymer including the structure unit represented by the following chemical formula 1 and the structure unit represented by the following chemical formula 2. The copolymer may furthermore optionally contain other structure units.

Due to the structure units, luminosity of the image and the strength of the hollow resin can be enhanced so that the hollow in the image can be maintained.

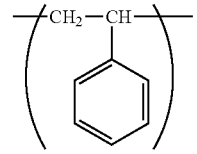

Chemical formula 1

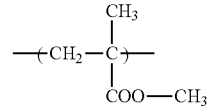

Chemical formula 2

There is no specific limitation to the other structure units and it can be suitably selected to suit to a particular application. A specific example is α-methyl styrene.

Since the copolymer includes the structure unit represented by the following chemical formula 1, luminosity of the image can be improved. Since the copolymer includes the structure unit represented by the following chemical formula 2, strength of the hollow resin can be improved.

The hollow resin particle contained in the ink includes an outer layer of resin and hollow inside. Since the inside (inner layer) is hollow, specific gravity as ink is about 1 so that, like titanium ink dioxide used as white color pigment, sedimentation of the hollow resin particle can be prevented.

The hollow resin particle contained in the ink corresponds to the hollow resin contained in the image.

In addition, the hollow resin particle preferably has an outer diameter of from 0.1 to 1 μm and an inner diameter of from 0.04 to 0.8 μm. When the outer diameter of the hollow resin particle is from 0.1 to 1 μm and the inner diameter of the hollow resin particle is from 0.04 to 0.8 μm, voids (hollow) can be formed in the image.

The average thickness of the resin in the hollow resin particle is preferably from 10 to 20 percent to the size of the entire hollow resin particle in order to prevent sedimentation of the resin particle over time. When the average thickness of the resin in the hollow resin particle is preferably from 10 to 20 percent to the size of the entire hollow resin particle, voids (hollow) can be formed in the image.

The ratio of the structure unit represented by the Chemical formula 1 to the structure unit represented by the Chemical formula 2 in the hollow resin in the image matches the ratio of the structure unit represented by the Chemical formula 1 to the structure unit represented by the Chemical formula 2 in the hollow resin particle in the ink.

The ratio of the structure unit represented by the Chemical formula 1 to the structure unit represented by the Chemical formula 2 can be calculated by taking the ratio of (Y/X) using IR spectra of the image, where X represents the absorbance of the image at the maximum absorption wavelength in a range of from 1,590 to 1,610 $cm^{-1}$ derived from the stretching vibration of C=C of the aromatic series of the structure unit represented by the Chemical formula 1 and Y represents the absorbance of the image at the maximum absorption wavelength in a range of from 1,720 to 1,740 $cm^{-1}$ derived from the stretching vibration of the carbonyl group in the structure unit represented by the Chemical formula 2.

The hollow resin particle contained in the ink preferably has a volume average particle diameter of from 400 to 800 nm. If the volume average particle diameter is 400 nm or greater, it is possible to secure luminosity for a recording medium such as high quality paper. When the volume average particle diameter is 800 nm or less, sedimentation property and discharging stability can be improved. The volume average particle diameter is the particle diameter at 50 percent of the accumulated curve when an accumulated curve is obtained as the entire volume of a group is defined as 100 percent.

The volume average particle diameter can be measured by, for example, a method of using a laser scattering/diffraction type particle size measuring device.

Whether the hollow resin particle includes the structure unit represented by the Chemical formula 1 illustrated above and the structure unit represented by the Chemical formula 2 illustrated above can be confirmed by structure analysis using microscopic Fourier-transform infrared spectroscopy (FT-IR) measuring device (iN10MX/iZ10, manufactured by Thermo Fisher Scientific K.K.) and analysis software (OMNIC).

The proportion of the hollow resin particle is preferably from 3 to 14 percent by mass and more preferably 5.0 to 12.5 percent by mass to the total mass of ink. If the proportion is 3 percent by mass or more, it is possible to secure luminosity for a recording medium such as high quality paper. When the proportion is 14 percent by mass of less, sedimentation property and discharging stability can be enhanced.

The proportion of the hollow resin to the total mass of the image is preferably from 50 to 100 percent by mass and more preferably from 60 to 80 percent by mass. The hollow resin to the total mass of the image can be measured by using, for example, microscopic FT-IR measuring device (iN10MX/iZ10, manufactured by Thermo Fisher Scientific K.K.) and analysis software (OMNIC).

The preparation method of the hollow resin particle has no particular limit and the hollow resin can be prepared by using any known method. It is possible to employ, for example, the so-called emulsion polymerization method in which vinyl monomers, surfactants, polymerization initiators, and aqueous dispersion medium are stirred while being heated in nitrogen atmosphere to form a hollow resin emulsion.

Examples of the vinyl monomer are mono-functional vinyl monomers, bi-functional vinyl monomers, and tri-functional vinyl monomers. These can be used alone or in combination.

An example of the mono-functional vinyl monomer is nonionic monoethylene unsaturated monomers.

Specific examples the nonionic monoethylene unsaturated monomers include, but are not limited to, styrene, vinyl toluene, ethylene, vinylacetate, vinyl chloride, vinylidene chloride, acrylonitrile, (meth)acrylamide, and (meth)acrylate. These can be used alone or in combination. Of these, (meth)acrylates are preferable.

Specific examples of the (meth)acrylate include, but are not limited to, methyl(meth)acrylate, ethyl(meth)acrylate, butyl(meth)acrylate, 2-hydroxyethyl(meth)acrylate, 2-ethylhexyl(meth)acrylate, benzyl(meth)acrylate, lauryl(meth)acrylate, oleyl(meth)acrylate, palmityl(meth)acrylate, and stearyl(meth)acrylate.

Specific examples of the bi-functional vinyl monomer include, but are not limited to, divinylbenzene, allylmethacrylate, ethylene glycol di(meth)acrylate, 1,5-butane diol di(meth)acrylate, and diethyleneglycol di(meth)acrylate.

A specific example of the tri-functional vinyl monomers is trimethylolpropane tri(meth)acrylate.

The mono-functional vinyl monomer mentioned above and the bi-functional vinyl monomer mentioned above are copolymerized for high level cross linking, so that a hollow resin particle having good light scattering property, heat resistance, chemical resistance, and solvent dispersibility is obtained.

As the surfactant, articles forming molecule aggregation such as micelle in water are suitable. Examples are anionic surfactants, non-ionic surfactants, cationic surfactants, and amphoteric surfactants. These can be used alone or in combination.

As the polymerization initiator, known water-soluble compounds are usable.

Specific examples include, but are not limited to, hydrogen peroxide and potassium persulfate. These can be used alone or in combination.

Examples of aqueous solvent medium are water and water containing a hydrophilic organic solvent.

Other Resins

The other resins are resins excluding hollow resins and have no particular limit and can be suitably selected to suit to a particular application. Examples are polyurethane resins, polyester resins, acrylic-based resins, vinyl acetate-based resins, styrene-based resins, butadiene-based resins, styrene-butadiene-based resins, vinylchloride-based resins, acrylic styrene-based resins, and acrylic silicone-based resins. These can be used alone or in combination. Of these, acrylic silicone-based resins and polyurethane resins are preferable.

To obtain the other resins, a resin emulsion in which resin particles are dispersed in water is mixed with materials such as an organic solvent. It is possible to use a suitably-synthesized resin particle as the other resin particle. Alternatively, it is available on the market. These can be used alone or in combination.

The glass transition temperature (Tg) of the other resin greatly affects fixability of an image if the image is dried after recording.

Therefore, the glass transition temperature (Tg) of the resin is preferably 0 degrees C. or below and more preferably from −45 to 0 degrees as acrylic silicone resin, and preferably 0 degrees C. or below and more preferably from −45 to 0 degrees as polyurethane resin.

If the ink contains the resin particle, the image containing the resin can be formed.

The volume average particle diameter of the resin particle is not particularly limited and can be suitably selected to suit to a particular application. The volume average particle diameter is preferably from 10 to 1,000 nm, more preferably from 10 to 200 nm, and furthermore preferably from 10 to 100 nm to obtain good fixability and image hardness.

The volume average particle diameter can be measured by using, for example, a particle size analyzer (Nanotrac Wave-UT151, manufactured by MicrotracBEL Corp.).

The proportion of the resin is not particularly limited and can be suitably selected to suit to a particular application. In terms of fixability and storage stability (ant-sedimentation) of ink, it is preferably from 1 to 10 percent by mass and more preferably from 3 to 5 percent by mass to the total mass of the ink.

The proportion of the resin to the total mass of the image is preferably from 21.4 to 33.3 percent by mass and more preferably from 25 to 30 percent by mass. The resin to the total mass of the image can be measured by using, for example, microscopic Fourier-transform infrared spectroscopy (FT-IR) measuring device (iN10MX/iZ10, manufactured by Thermo Fisher Scientific K.K.) and analysis software (OMNIC).

The image can be formed using ink containing the hollow resin particle.

The ink preferably contains an organic solvent, water, and a resin. It may furthermore optionally contain a coloring material and other components.

Organic Solvent

The organic solvent preferably has a mixture SP value of from 11.0 to 15.5 $(cal/cm^3)^{0.5}$. The mixing SP value is calculated from solubility parameter (SP) of the organic solvents in ink. When the mixing SP value is 11.0 $(cal/cm^3)^{0.5}$ or greater, it is possible to suppress dissolution of a resin in the hollow resin particle by the organic solvent. Conversely, when the mixing SP value is 15.5 $(cal/cm^3)^{0.5}$ or less, fixability is prevented from deteriorating caused by poor drying.

When calculating the mixing SP value of the organic solvents in ink, the organic solvents except for water are used for the calculation.

The SP value can be obtained by Hansen solubility parameter.

In addition, the mixing SP value of the organic solvents contained in ink is calculated by the following relation.

Mixing SP value $(cal/cm^3)^{0.5}$ of organic solvents in ink=[SP value of organic solvent $A$×volume ratio of organic solvent $A$]+ . . . +[SP value of organic solvent $n$×volume ratio of organic solvent $n$]

In addition, although the organic solvent for use in the present disclosure includes articles classified as permeating agents, defoaming agents, etc. in terms of functionality, only the organic solvent accounting for 3 percent by mass or more of the ink is counted in the above-mentioned calculation of the mixing SP value. In addition, if only a single organic solvent is used, the SP value of the organic solvent is defined as the mixing SP value.

Examples of the organic solvent are polyols, ethers such as polyol alkylethers and polyol arylethers, nitrogen-containing heterocyclic compounds, amides, amines, and sulfur-containing compounds. These can be used alone or in combination.

Specific examples of the organic solvent include, but are not limited to, polyols such as ethylene glycol, diethylene glycol, 1,2-propanediol, 1,3-propanediol, 1,2-butanediol, 1,3-butanediol, 1,4-butanediol, 2,3-butanediol, 3-methyl-1,3-butane diol, triethylene glycol, polyethylene glycol, polypropylene glycol, 1,2-pentanediol, 1,3-pentanediol, 1,4-pentanediol, 2,4-pentanediol, 1,5-pentanediol, 1,2-hexanediol, 1,6-hexanediol, 1,3-hexanediol, 2,5-hexanediol, 1,5-hexanediol, glycerin, 1,2,6-hexanetriol, 2-ethyl-1,3-hexanediol, ethyl-1,2,4-butane triol, 1,2,3-butanetriol, 2,2,4-trimethyl-1,3-pentanediol, and petriol; polyol alkylethers such as ethylene glycol monoethylether, ethylene glycol monobutylether, diethylene glycol monomethylether, diethylene glycol monoethylether, diethylene glycol monobutylether, tetraethylene glycol monomethylether, and propylene glycol monoethylether; polyol arylethers such as ethylene glycol monophenylether and ethylene glycol monobenzylether; nitrogen-containing heterocyclic compounds such as 2-pyrolidone, N-methyl-2-pyrolidone, N-hydroxyethyl-2-pyrolidone, 1,3-dimethyl-2-imidazolidinone, ε-caprolactam, and γ-butyrolactone; amides such as formamide, N-methylformamide, N,N-dimethylformamide, 3-methoxy-N,N-dimethyl propioneamide, and 3-buthoxy-N,N-dimethyl propioneamide; amines such as monoethanolamine, diethanolamine, and triethylamine; sulfur-containing compounds such as dimethyl sulfoxide, sulfolane, and thiodiethanol; propylene carbonate, and ethylene carbonate.

To serve as a humectant and impart a good drying property, the organic solvent preferably has a boiling point of 300 degrees C. or lower and more preferably 250 degrees C. or lower.

In addition, using an organic solvent having a boiling point of from 150 to 300 degrees C. is preferable to improve fixability.

The hydrogen bond terms of Hansen solubility parameter (HSP) organic solvent is preferably from 3 to 6.8 $(cal/cm^3)^{0.5}$.

The hydrogen bond term can be obtained according to the atomic group aggregation method of treating organic molecules as atomic groups, which is proposed by Krevelen (Krevelen, Properties of Polymer, Second edition, New York, 154 (1976).

Examples of the organic solvents satisfying the conditions mentioned above are glycerin, 1,2-propanediol, 1,3-propanediol, 1,2-butanediol, 1,3-butanediol, isoprene glycol, and oxetane compounds.

An example of the oxetane compound is 3-ethyl-3-hydroxymethyl oxetane.

Polyol compounds having eight or more carbon atoms and glycol ether compounds are also suitable.

Specific examples of the polyol compounds having eight or more carbon atoms include, but are not limited to, 2-ethyl-1,3-hexanediol and 2,2,4-trimethyl-1,3-pentanediol.

Specific examples of the glycolether compounds include, but are not limited to, polyol alkylethers such as ethyleneglycol monoethylether, ethyleneglycol monobutylether, diethyleneglycol monomethylether, diethyleneglycol monoethylether, diethyleneglycol monobutylether, tetraethyleneglycol monomethylether, and propyleneglycol monoethylether; and polyol arylethers such as ethyleneglycol monophenylether and ethyleneglycol monobenzyl ether.

The polyol compounds having eight or more carbon atoms and glycolether compounds enhance permeability of ink when paper is used as a print medium (recording medium).

The proportion of the organic solvent in ink has no particular limit and can be suitably selected to suit to a particular application.

In terms of the drying property and discharging reliability of the ink, the proportion is preferably from 10 to 60 percent by mass and more preferably 20 to 60 percent by mass.

Wax

The wax mentioned above is capable of imparting slippage to an image.

Of the wax, polyethylene wax and carnauba wax are preferable in terms of film forming property and slippage in particular when an ink is applied to an image forming portion.

The melting point of the wax is preferably from 80 to 140 degrees C. and more preferably from 100 to 140 degrees C. When the melting point is 80 degrees C. or higher, wax does not excessively melt or coagulate even in a room temperature environment, so that storage stability of the ink is maintained. When the melting point is 140 degrees C. or lower, wax melts sufficiently in a room temperature environment, so that slippage is imparted to the ink.

The volume average particle diameter of the wax is preferably 0.01 µm or greater and more preferably from 0.01 to 0.1 µm. When the volume average particle diameter is 0.01 µm or greater, wax particles tend to be oriented to the surface of an image, which makes it possible to impart slippage to ink.

The volume average particle diameter can be measured by, for example, a method of using a laser scattering/diffraction type particle size measuring device.

The polyethylene-based wax is available on the market. Examples of such product are High-Tech series, manufactured by TOHO Chemical Industry Co., Ltd. and AQUACER SERIFS, manufactured by BYK are suitable. These can be used alone or in combination.

The carnauba wax is available on the market. Examples of such products are Selosol 524 and Trasol CN (both manufactured by CHUKYO YUSHI CO., LTD.) are suitable. These can be used alone or in combination.

The proportion of the wax to the total mass of the image is preferably from 1 to 10 percent by mass and more preferably 1 to 5 percent by mass.

Water

The proportion of water in the ink is not particularly limited and can be suitably selected to suit to a particular application. For example, in terms of the drying property and discharging reliability of the ink, the proportion is preferably from 10 to 90 percent by mass and more preferably from 20 to 60 percent by mass.

Property of Ink

Properties of the ink are not particularly limited and can be suitably selected to suit to a particular application. For example, viscosity, surface tension, pH, etc, are preferable if those are in the following ranges.

Viscosity of the ink at 25 degrees C. is preferably from 5 to 30 mPa·s and more preferably from 5 to 25 mPa·s to improve print density and text quality and obtain good dischargeability. Viscosity can be measured by, for example, a rotatory viscometer (RE-80L, manufactured by TOKI SANGYO CO., LTD.). The measuring conditions are as follows:

Standard cone rotor (1°34'×R24)
Sample liquid amount: 1.2 mL
Number of rotations: 50 rotations per minute (rpm)
25 degrees C.
Measuring time: three minutes The dynamic surface tension of the ink is preferably form 20 to 35 mN/m at 25 degrees C. when the bubble life time is 1,500 ms in terms that the ink is suitably levelized on a recording medium and the drying time of the ink is shortened. The dynamic surface tension can be measured by, for example, a maximum bubble pressure technique at 25 degrees C. using a dynamic surface tensiometer (SITA DynoTester, manufactured by SITA Messtechnik GmbH).

"Bubble life time" is life length of a foam produced according to maximum bubble pressure technique and is also referred to as "surface life length", which is a time from when a new interface is produced in a probe front end in a dynamic surface tensiometer until the maximum bubble pressure.

pH of the ink is preferably from 7 to 12 and more preferably from 8 to 11 in terms of preventing metal material in contact with liquid from being corroded. pH can be measured by a pH meter (HM-30R, manufactured by DKK-TOA CORPORATION) and the temperature of ink is set to be 25 degrees C.

The ink used to form the image can be used as white ink. When the recording medium is transparent, white ink is used to form a backdrop as the image. Color ink such as yellow, magenta, cyan, and black are used to print on the image of the backdrop. To obtain such color ink, a coloring material is added.

The white ink is not only used for forming a backdrop but also for forming a overlapping layer. For example, color ink is used to print an image on the recording medium and thereafter white ink is applied onto the color ink to form an image.

White ink can be applied to the entire portion of the recording medium or only the image formed with the color ink. In addition, it can be applied to a portion overlapping with the image using the color ink.

The coloring material for use in the color ink is as follows.

Coloring Material

The coloring material has no particular limit. For example, pigments and dyes are suitable.

As the pigment, both inorganic pigments and organic pigments can be used. These can be used alone or in combination. In addition, it is possible to use a mixed crystal.

As the pigments, for example, black pigments, yellow pigments, magenta pigments, cyan pigments, white pigments, green pigments, orange pigments, gloss pigments of gold, silver, etc., and metallic pigments can be used.

As the inorganic pigments, in addition to titanium oxide, iron oxide, calcium carbonate, barium sulfate, aluminum hydroxide, barium yellow, cadmium red, and chrome yellow, carbon black manufactured by known methods such as contact methods, furnace methods, and thermal methods can be used.

As the organic pigments, it is possible to use azo pigments, polycyclic pigments (phthalocyanine pigments, perylene pigments, perinone pigments, anthraquinone pigments, quinacridone pigments, dioxazine pigments, indigo pigments, thioindigo pigments, isoindolinone pigments, and quinophthalone pigments, etc.), dye chelates (basic dye type chelates, acid dye type chelates, etc.), nitro pigments, nitroso pigments, and aniline black can be used. Of those pigments, pigments having good affinity with solvents are preferable. Also, hollow resin particles and hollow inorganic particles can be used.

Specific examples of the pigments for black include, but are not limited to, carbon black (C.I. Pigment Black 7) such as furnace black, lamp black, acetylene black, and channel black, metals such as copper, iron (C.I. Pigment Black 11), and titanium oxide, and organic pigments such as aniline black (C.I. Pigment Black 1).

Specific examples of the pigments for color include, but are not limited to, C.I. Pigment Yellow 1, 3, 12, 13, 14, 17, 24, 34, 35, 37, 42 (yellow iron oxide), 53, 55, 74, 81, 83, 95, 97, 98, 100, 101, 104, 108, 109, 110, 117, 120, 138, 150, 153, 155, 180, 185, and 213; C.I. Pigment Orange 5, 13, 16, 17, 36, 43, and 51; C.I. Pigment Red 1, 2, 3, 5, 17, 22, 23, 31, 38, 48:2, 48:2 {Permanent Red 2B(Ca)}, 48:3, 48:4, 49:1, 52:2, 53:1, 57:1 (Brilliant Carmine 6B), 60:1, 63:1, 63:2, 64:1, 81, 83, 88, 101 (rouge), 104, 105, 106, 108 (Cadmium Red), 112, 114, 122 (Quinacridone Magenta), 123, 146, 149, 166, 168, 170, 172, 177, 178, 179, 184, 185, 190, 193, 202, 207, 208, 209, 213, 219, 224, 254, and 264; C.I. Pigment Violet 1 (Rohdamine Lake), 3, 5:1, 16, 19, 23, and 38; C.I. Pigment Blue 1, 2, 15 (Phthalocyanine Blue), 15:1, 15:2, 15:3, 15:4, (Phthalocyanine Blue), 16, 17:1, 56, 60, and 63; C.I. Pigment Green 1, 4, 7, 8, 10, 17, 18, and 36.

The type of dye is not particularly limited and includes, for example, acidic dyes, direct dyes, reactive dyes, basic dyes. These can be used alone or in combination.

Specific examples of the dye include, but are not limited to, C.I. Acid Yellow 17, 23, 42, 44, 79, and 142, C.I. Acid Red 52, 80, 82, 249, 254, and 289, C.I. Acid Blue 9, 45, and 249, C.I. Acid Black 1, 2, 24, and 94, C.I. Food Black 1 and 2, C.I. Direct Yellow 1, 12, 24, 33, 50, 55, 58, 86, 132, 142, 144, and 173, C.I. Direct Red 1, 4, 9, 80, 81, 225, and 227, C.I. Direct Blue 1, 2, 15, 71, 86, 87, 98, 165, 199, and 202, C.I. Direct Black 19, 38, 51, 71, 154, 168, 171, and 195, C.I. Reactive Red 14, 32, 55, 79, and 249, and C.I. Reactive Black 3, 4, and 35.

The proportion of the coloring material in the ink is preferably from 0.1 to 15 percent by mass and more preferably from 1 to 10 percent by mass in terms of enhancement of image density, fixability, and discharging stability.

To obtain an ink by dispersing a pigment, for example, a hydrophilic functional group is introduced into a pigment to prepare a self-dispersible pigment, the surface of a pigment is coated with a resin followed by dispersion, or a dispersant is used to disperse a pigment.

To prepare a self-dispersible pigment by introducing a hydrophilic functional group into a pigment, for example, it is possible to add a functional group such as sulfone group and carboxyl group to the pigment (e.g., carbon) to disperse the pigment in water.

To coat the surface of a pigment with a resin, the pigment is encapsulated by microcapsules to make the pigment dispersible in water. This can be referred to as a resin-coated pigment. In this case, all the pigments to be added to ink are not necessarily entirely coated with a resin. Pigments partially or wholly uncovered with a resin may be dispersed in the ink unless such pigments have an adverse impact.

In a method of using a dispersant to disperse a pigment, for example, a known dispersant of a small molecular weight or a large molecular weight, which is represented by a surfactant, is used to disperse the pigment in ink.

As the dispersant, it is possible to use, for example, an anionic surfactant, a cationic surfactant, a nonionic surfactant, an amphoteric surfactant, etc. depending on a pigment.

Also, a nonionic surfactant (RT-100, manufactured by TAKEMOTO OIL & FAT CO., LTD.) and a formalin condensate of naphthalene sodium sulfonate are suitable as the dispersant.

Those can be used alone or in combination.

Pigment Dispersion

The ink can be obtained by mixing a pigment with materials such as water and an organic solvent. It is also possible to firstly mix a pigment with water, a dispersant, etc., to prepare a pigment dispersion and thereafter mix the pigment dispersion with materials such as water and an organic solvent to manufacture an ink.

The pigment dispersion is obtained by mixing and dispersing water, a pigment, a pigment dispersant, and other optional components and adjusting the particle size. It is good to use a dispersing device for dispersion.

The particle diameter of the pigment in the pigment dispersion has no particular limit. For example, the maximum frequency is preferably from 20 to 500 nm and more preferably from 20 to 150 nm in the maximum number conversion to improve dispersion stability of the pigment and ameliorate discharging stability and the image quality such as image density. The particle diameter of a pigment can be measured using a particle size analyzer (Nanotrac Wave-UT151, manufactured by MicrotracBEL Corp).

In addition, the proportion of the pigment in the pigment dispersion is not particularly limited and can be suitably selected to suit a particular application. In terms of improving discharging stability and image density, the proportion is preferably from 0.1 to 50 percent by mass and more preferably from 0.1 to 30 percent by mass.

It is preferable that the pigment dispersion be filtered with a filter, a centrifuge, etc. to remove coarse particles followed by degassing.

Other Components

The ink may further optionally include a surfactant, a defoaming agent, a preservative and fungicide, a corrosion inhibitor, a pH regulator, etc.

Surfactant

Examples of the surfactant are silicone-based surfactants, fluorochemical surfactants, amphoteric surfactants, nonionic surfactants, anionic surfactants, etc.

The silicone-based surfactant has no specific limit and can be suitably selected to suit to a particular application.

Of these, preferred are silicone-based surfactants which are not decomposed even in a high pH environment.

Specific examples thereof include, but are not limited to, side-chain-modified polydimethylsiloxane, both-distal-end-modified polydimethylsiloxane, one-distal-end-modified polydimethylsiloxane, and side-chain-both-distal-end-modified polydimethylsiloxane. A silicone-based surfactant having a polyoxyethylene group or a polyoxypropylene group as a modification group is particularly preferable because such an agent demonstrates good properties as an aqueous surfactant. It is possible to use a polyether-modified silicone-based surfactant as the silicone-based surfactant.

A specific example is a compound in which a polyalkylene oxide structure is introduced into the side chain of the Si site of dimethyl silooxane.

Specific examples of the fluorochemical surfactants include, but are not limited to, perfluoroalkyl sulfonic acid compounds, perfluoroalkyl carboxylic acid compounds, ester compounds of perfluoroalkyl phosphoric acid, adducts of perfluoroalkyl ethylene oxide, and polyoxyalkylene ether polymer compounds having a perfluoroalkyl ether group in its side chain. These are particularly preferable because they do not easily produce foams.

Specific examples of the perfluoroalkyl sulfonic acid compounds include, but are not limited to, perfluoroalkyl sulfonic acid and salts of perfluoroalkyl sulfonic acid.

Specific examples of the perfluoroalkyl carboxylic acid compounds include, but are not limited to, perfluoroalkyl carboxylic acid and salts of perfluoroalkyl carboxylic acid.

Specific examples of the polyoxyalkylene ether polymer compounds having a perfluoroalkyl ether group in its side chain include, but are not limited to, salts of sulfuric acid ester of polyoxyalkylene ether polymer having a perfluoroalkyl ether group in its side chain and salts of polyoxyalkylene ether polymers having a perfluoroalkyl ether group in its side chain. Counter ions of salts in these fluorochemical surfactants are, for example, Li, Na, K, $NH_4$, $NH_3CH_2CH_2OH$, $NH_2(CH_2CH_2OH)_2$, and $NH(CH_2CH_2OH)_3$.

Specific examples of the amphoteric surfactants include, but are not limited to, lauryl aminopropionic acid salts, lauryl dimethyl betaine, stearyl dimethyl betaine, and lauryl dihydroxyethyl betaine.

Specific examples of the nonionic surfactants include, but are not limited to, polyoxyethylene alkyl phenyl ethers, polyoxyethylene alkyl esters, polyoxyethylene alkyl amines, polyoxyethylene alkyl amides, polyoxyethylene propylene block polymers, sorbitan aliphatic acid esters, polyoxyethylene sorbitan aliphatic acid esters, and adducts of acetylene alcohol with ethylene oxides.

Specific examples of the anionic surfactants include, but are not limited to, polyoxyethylene alkyl ether acetates, dodecyl benzene sulfonates, laurates, and polyoxyethylene alkyl ether sulfates.

These can be used alone or in combination.

The silicone-based surfactants has no particular limit and can be suitably selected to suit to a particular application. Specific examples thereof include, but are not limited to, side-chain-modified polydimethyl siloxane, both distal-end-modified polydimethylsiloxane, one-distal-end-modified polydimethylsiloxane, and side-chain-both-distal-end-modified polydimethylsiloxane. In particular, a polyether-modified silicone-based surfactant having a polyoxyethylene group or a polyoxyethylene polyoxypropylene group is particularly preferable because such a surfactant demonstrates good characteristics as an aqueous surfactant.

Any suitably synthesized surfactant and any product thereof available on the market is suitable. Products available on the market can be obtained from Byc Chemie Japan Co., Ltd., Shin-Etsu Silicone Co., Ltd., Dow Corning Toray Co., Ltd., etc., NIHON EMULSION Co., Ltd., Kyoeisha Chemical Co., Ltd., etc.

The polyether-modified silicon-based surfactant has no particular limit and can be suitably selected to suit to a particular application. For example, a compound is usable in which the polyalkylene oxide structure represented by the following Chemical formula S-1 is introduced into the side chain of the Si site of dimethyl polysiloxane.

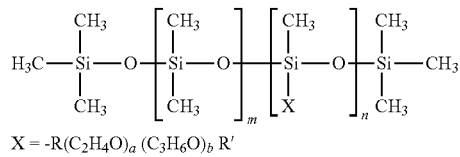

Chemical formula S-1

$X = -R(C_2H_4O)_a (C_3H_6O)_b R'$

In the Chemical formula S-1, "m", "n", "a", and "b" each, respectively independently represent integers, R represents an alkylene group, and R' represents an alkyl group.

Specific examples of polyether-modified silicone-based surfactants include, but are not limited to, KF-618, KF-642, and KF-643 (all manufactured by Shin-Etsu Chemical Co., Ltd.), EMALEX-SS-5602 and SS-1906EX (both manufactured by NIHON EMULSION Co., Ltd.), FZ-2105, FZ-2118, FZ-2154, FZ-2161, FZ-2162, FZ-2163, and FZ-2164 (all manufactured by Dow Corning Toray Co., Ltd.), BYK-33 and BYK-387 (both manufactured by BYK Japan KK.), and TSF4440, TSF4452, and TSF4453 (all manufactured by Momentive Performance Materials Inc.).

A fluorochemical surfactant in which the number of carbon atoms replaced with fluorine atoms is 2-16 is preferable and, 4 to 16, more preferable.

Specific examples of the fluorochemical surfactants include, but are not limited to, perfluoroalkyl phosphoric acid ester compounds, adducts of perfluoroalkyl ethylene oxide, and polyoxyalkylene ether polymer compounds having a perfluoroalkyl ether group in its side chain. Of these, polyoxyalkylene ether polymer compounds having a perfluoroalkyl ether group in its side chain are preferable because they do not foam easily and the fluorosurfactant represented by the following Chemical formula F-1 or Chemical formula F-2 is more preferable.

$CF_3CF_2(CF_2CF_2)_m-CH_2CH_2O(CH_2CH_2O)_nH$  Chemical formula F-1

In the Chemical formula F-1, "m" is preferably 0 or an integer of from 1 to 10 and "n" is preferably 0 or an integer of from 1 to 40.

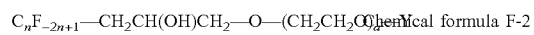

$C_nF_{-2n+1}-CH_2CH(OH)CH_2-O-(CH_2CH_2O)_a H$  Chemical formula F-2

In the compound represented by the chemical formula F-2, Y represents H or $CmF_{2m+1}$, where m represents an integer of from 1 to 6, or $CH_2CH(OH)CH_2-CmF_{2m+1}$, where m represents an integer of from 4 to 6, or $CpH_{2p+1}$, where p is an integer of from 1 to 19. "n" represents an integer of from 1 to 6. "a" represents an integer of from 4 to 14.

As the fluorochemical surfactant, products available on the market may be used. Specific examples include, but are not limited to, SURFLON S-111, SURFLON S-112, SURFLON S-121, SURFLON S-131, SURFLON S-132, SURFLON S-141, and SURFLON S-145 (all manufactured by ASAHI GLASS CO., LTD.); FLUORAD FC-93, FC-95, FC-98, FC-129, FC-135, FC-170C, FC-430, and FC-431 (all manufactured by SUMITOMO 3M); MEGAFACE F-470, F-1405, and F-474 (all manufactured by DIC CORPORATION); ZONYL TBS, FSP, FSA, FSN-100, FSN, FSO-100, FSO, FS-300, UR, and Capstone™ FS-30, FS-31, FS-3100, FS-34, and FS-35 (all manufactured by The Chemours Company); FT-110, FT-250, FT-251, FT-400S, FT-150, and FT-400SW (all manufactured by NEOS COMPANY LIMITED); POLYFOX PF-136A, PF-156A, PF-151N, PF-154, and PF-159 (manufactured by OMNOVA SOLUTIONS INC.); and UNIDYNE™ DSN-403N (manufactured by DAIKIN INDUSTRIES, Ltd.). Of these, in terms of improvement on print quality, in particular coloring property and permeability, wettability, and uniform dying property on paper, FS-3100, FS-34, and FS-300 of The Chemours Company, FT-110, FT-250, FT-251, FT-400S, FT-150, and FT-400SW of NEOS COMPANY LIMITED, POLYFOX PF-151N of OMNOVA SOLUTIONS INC., and UNIDYNE™ DSN-403N (manufactured by DAIKIN INDUSTRIES, Ltd.) are particularly preferable.

The proportion of the surfactant in ink is not particularly limited and can be suitably selected to suit to a particular application. It is preferably from 0.001 to 5 percent by mass and more preferably from 0.05 to 5 percent by mass in terms of enhancement of wettability and discharging stability and improvement on image quality.

Defoaming Agent

The defoaming agent has no particular limit. For example, silicon-based defoaming agents, polyether-based defoaming agents, and aliphatic acid ester-based defoaming agents are suitable. These can be used alone or in combination. Of these, silicone-based defoaming agents are preferable in terms of the effect of breaking foams.

Preservatives and Fungicides

The preservatives and fungicides are not particularly limited. A specific example is 1,2-benzisothiazoline-3-one.

Corrosion Inhibitor

The corrosion inhibitor has no particular limitation. Examples are acid sulfites and sodium thiosulfates.

pH Regulator

The pH regulator has no particular limit. It is preferable to adjust the pH to be from 7 or higher.

Specific examples include, but are not limited to, amines such as diethanol amine and triethanol amine.

Ink for Manufacturing Recorded Matter

The ink for manufacturing the recorded matter of the present disclosure includes a hollow resin particle containing a copolymer including the structure unit represented by the following chemical formula 1 and the structure unit represented by the following chemical formula 2, an organic solvent, and water. In an IR spectrum of the hollow resin particle, the hollow resin particle satisfies the following ratio: $3.0 \leq Y/X \leq 6.0$, where X represents the absorbance of the hollow resin particle of the maximum absorption wavelength in a range of from 1,590 to 1,610 $cm^{-1}$ and Y represents the absorbance of the hollow resin particle of the maximum absorption wavelength in a range of from 1,720 to 1,740 $cm^{-1}$.

The ink is used for manufacturing the recorded matter of the present disclosure.

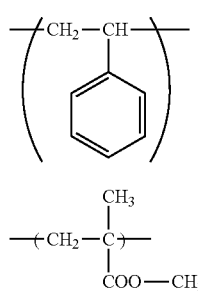

Chemical formula 1

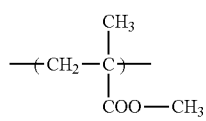

Chemical formula 2

The mixing SP value of the organic solvent is preferably from 10.4 to 16.0 $(cal/cm^3)^{0.5}$.

Since the ink for manufacturing the recorded matter includes a hollow resin particle including a copolymer including the structure unit represented by the following chemical formula 1 and the structure unit represented by the following chemical formula 2, it is possible to manufacture recorded matter having voids (hollow) derived from the hollow resin particle in the image. The hollow resin in the recorded matter is configured to have multiple fine voids (hollow) in the resin.

The ink mentioned above can be used as the ink for manufacturing the recorded matter.

Pre-Processing Fluid

The pre-processing fluid includes a flocculant, an organic solvent, water, and optional materials such as a surfactant, a defoaming agent, a pH regulator, a preservatives and fungicides, and a corrosion inhibitor.

The organic solvent, the surfactant, the defoaming agent, the pH regulator, the preservatives and fungicides, and the corrosion inhibitor can be the same material as those for use in the ink. Also, other materials for use in known processing fluid can be used.

The type of the flocculant is not particularly limited. For example, water-soluble cationic polymers, acids, and multi-valent metal salts are suitable.

Post-Processing Fluid

The post-processing fluid has no particular limit. It is preferable that the post-processing fluid can form a transparent layer. Materials such as organic solvents, water, resins, surfactants, defoaming agents, pH regulators, preservatives and fungicides, corrosion inhibitors, etc. are suitably selected based on a necessity basis and mixed to obtain the post-processing fluid. The post-processing fluid can be applied to the entire recording area formed on a recording medium or only the area on which an ink image is formed.

Recording Medium

The recording medium is not particularly limited. Plain paper, gloss paper, special paper, cloth, etc. are usable. Also, good images can be formed on a non-permeable substrate.

The non-permeable substrate has a surface with low moisture permeability and absorbency and includes a material having myriad of hollow spaces inside but not open to the outside. To be more quantitative, the substrate has a water-absorption amount of 10 $mL/m^2$ or less from the start of the contact until 30 $msec^{1/2}$ later according to Bristow method.

For example, plastic films such as polyvinyl chloride resin film, polyethylene terephthalate (PET) film, polypropylene film, polyethylene film, and polycarbonate film are suitably used as the non-permeable substrate.

The recording medium is not limited to articles used as typical recording media. It is suitable to use building materials such as wall paper, floor material, and tiles, cloth for apparel such as T-shirts, textile, and leather as the recording medium. In addition, the configuration of the paths through which the recording medium is conveyed can be adjusted to use ceramics, glass, metal, etc.

Hereinafter, an example in which black (K), cyan (C), magenta (M), and yellow (Y) are used is described. In addition, it is possible to use ink including the hollow resin particle in place of or in addition to those.

Recording Device and Recording Method

The ink of the present disclosure is applicable to various recording devices employing an inkjet recording method, such as printers, facsimile machines, photocopiers, multifunction peripherals (serving as a printer, a facsimile machine, and a photocopier), and 3D model manufacturing devices (3D printers, additive manufacturing device, etc.).

In the present disclosure, the recording device and the recording method respectively represent a device capable of discharging ink, various processing fluids, etc. to a recording medium and a method of conducting recording utilizing the device. The recording medium means an article to which ink or various processing fluids can be attached even temporarily.

The recording device may further optionally include a device relating to feeding, conveying, and ejecting the recording medium and other devices referred to as a pre-processing device, a post-processing device, etc. in addition to the head portion to discharge the ink.

The recording device and the recording method may further optionally include a heater for use in the heating process and a drier for use in the drying process. For example, the heating device and the drying device include devices including heating and drying the print surface of a recording medium and the opposite surface thereof. The heating device and the drying device are not particularly limited. For example, a fan heater and an infra-red heater can be used. Heating and drying can be conducted before, in the middle of, or after printing.

The heating temperature is preferably from 100 to 200 degrees C. and more preferably from 120 to 150 degrees C.

In addition, the recording device and the recording method are not limited to those producing meaningful visible images such as texts and figures with the ink. For example, the print method and the recording device can produce patterns like geometric design and 3D images.

In addition, the recording device includes both a serial type device in which the liquid discharging head is caused to move and a line type device in which the liquid discharging head is not moved, unless otherwise specified.

Furthermore, in addition to the desktop type, this recording device includes a device capable of printing images on a wide recording medium such as A0 and a continuous printer capable of using continuous paper rolled up in a roll form as recording media.

Figure 2:
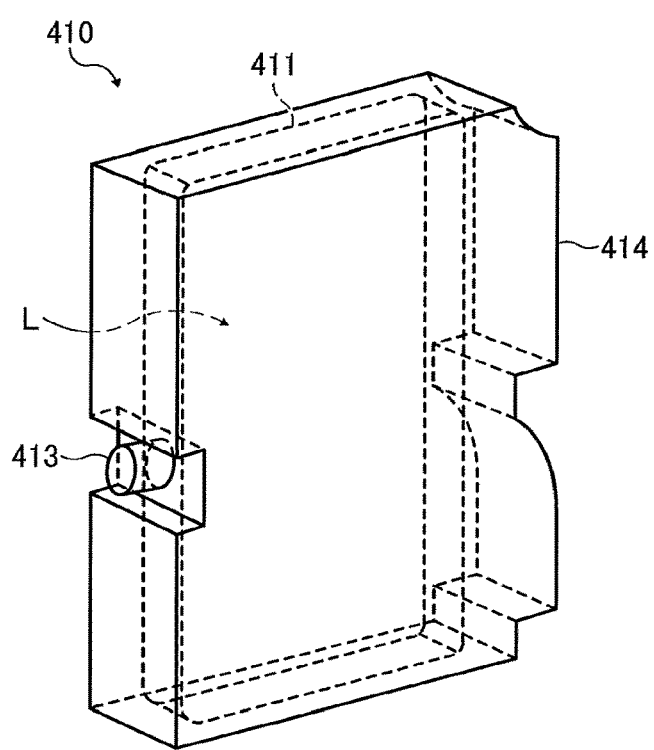
FIG. 2 is a diagram illustrating a perspective view of an example of a main tank of an inkjet recording device.

The recording (print) device is described using an example with reference to FIG. 1 and FIG. 2. FIG. 1 is a diagram illustrating a perspective view of the recording device. FIG. 2 is a diagram illustrating a perspective view of the main tank. An image forming apparatus 400 as an embodiment of the recording device is a serial type image forming apparatus. A mechanical unit 420 is disposed in an exterior 401 of the image forming apparatus 400. Each ink accommodating unit (ink container) 411 of each main tank 410 (410k, 410c, 410m, and 410y) for each color of black (K), cyan (C), magenta (M), and yellow (Y) is made of a packaging member such as aluminum laminate film. The ink accommodating unit 411 is accommodated in, for example, a plastic container housing unit 414.

As a result, the main tank 410 is used as an ink cartridge of each color.

A cartridge holder 404 is disposed on the rear side of the opening when a cover 401c is opened. The cartridge holder 404 is detachably attached to the main tank 410. As a result, each ink discharging outlet 413 of the main tank 410 communicates with a discharging head 434 for each color via a supplying tube 436 for each color so that the ink can be discharged from the discharging head 434 to a recording medium.

This recording device may include not only a portion to discharge ink but also a device referred to as a pre-processing device, a post-processing device, etc.

As an example of the pre-processing device and the post-processing device, as in the case of the ink such as black (K), cyan (C), magenta (M), and yellow (Y), the pre-processing device and the post-processing device may further include a liquid accommodating unit including a pre-processing fluid and/or a post-processing fluid to discharge the pre-processing fluid and/or the post-processing fluid according to an inkjet printing method.

As another example of the pre-processing device and the post-processing device, it is suitable to dispose a pre-processing device and a post-processing device which do not employ the inkjet printing method but a blade coating method, a roll coating method, or a spray coating method.

How to use the ink is not limited to the inkjet printing method. Specific examples of such methods other than the inkjet printing method include, but are not limited to, blade coating methods, gravure coating methods, bar coating methods, roll coating methods, dip coating methods, curtain coating methods, slide coating methods, die coating methods, and spray coating methods.

The usage of the ink of the present disclosure is not particularly limited and can be suitably selected to suit to a particular application. For example, the ink can be used for printed matter, a paint, a coating material, and foundation. The ink can be used to form two-dimensional texts and images and furthermore a three-dimensional solid object (3D modeling object) as a material for 3D modeling.

An apparatus for manufacturing a solid freeform fabrication to fabricate a three-dimensional solid object can be any known device with no particular limit. For example, the apparatus includes an ink container, a supplying device, and a discharging device, a drier, etc. The three-dimensional solid object includes an object manufactured by repeated ink coating. In addition, the three-dimensional solid object can be manufactured by processing a structure having a substrate such as a print medium to which the ink is applied as a molded processed product. The molded processed product is fabricated from printed matter or a structure having a sheet-like form, film-like form, etc. by, for example, heating drawing or punching. The molded processed product is suitably used for articles which are molded after surface-decorating. Examples thereof are gauges or operation panels of vehicles, office machines, electric and electronic devices, cameras, etc.

Having generally described preferred embodiments of this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

Next, embodiments of the present disclosure are described in detail with reference to Examples but not limited thereto.

Absorbance of the hollow resin particle in ink, mixing SP value of the organic solvent in ink, and the proportion of the resin to the image are measured in the following manner.

Absorbance

Absorbance X of the hollow resin particle at the maximum absorption wavelength in a range of from 1,590 to 1,610 $cm^{-1}$ and absorbance Y represents the absorbance thereof at the maximum absorption wavelength in a range of from 1,720 to 1,740 $cm^{-1}$ were measured by using microscopic FT-IR measuring device (iN10MX/iZ10, manufactured by Thermo Fisher Scientific K.K.) and analysis software (OMNIC). The ratio (Y/X) was calculated from the obtained values.

Mixing SP Value

The mixing SP value of the organic solvent in ink was calculated according to the following relation. In addition, in the calculation of the mixing SP value, only the organic solvents accounting for 3 percent by mass or more of the entire of image (ink) were included. In addition, water in the organic solvents were excluded from the calculation.

Mixing SP value $(cal/cm^3)^{0.5}$ of organic solvents in ink=[SP value of organic solvent A×volume ratio of organic solvent A]+ . . . +[SP value of organic solvent n×volume ratio of organic solvent n]

Content (Proportion) of Resin to Image

The resin to the image was measured by using microscopic FT-IR measuring device (iN10MX/iZ10, manufactured by Thermo Fisher Scientific K.K.) and analysis software (OMNIC).

Preparation Example 1 of Hollow Resin Particle

Preparation of Hollow Resin Particle B
1. Synthesis of Seed Particle Emulsion
726.0 parts of deionized water, 5.0 parts of methylmethacrylate, and 0.1 parts of methacrylic acid were charged in a four-necked separable flask equipped with a stiffer, a thermometer, a condenser, and a dripping funnel and thereafter heated while being stirred. When the internal temperature of the separable flask reached 70 degrees C., 1.0 parts of 10 percent by mass ammonium persulfate aqueous solution was added and the system was heated at 80 degrees C. for 20 minutes. 141.0 parts of methyl methacrylate, 94.9 parts of metharylic acid, 5.0 parts of alkylbenzene sodium sulfonate (Neogen SF-20, manufactured by DKS Co. Ltd.) as anionic emulsifier, and 120.0 parts of deionized water were emulsified by a homo disperser to prepare a pre-emulsion. Thereafter, the pre-emulsion was charged in the dripping funnel.

Next, while keeping the internal temperature of the separable flask at 80 degrees C., the thus-prepared pre-emulsion was uniformly dripped in three hours and at the same time, 10.0 parts of 10 percent ammonium persulfate aqueous solution was uniformly dripped in three hours. Subsequent to completion of the dripping, the resultant was aged at 80 degrees C. for three hours followed by cooling-down and filtrated by a filter cloth with 120 mesh to obtain a seed particle emulsion B.

2. Synthesis of Hollow Resin Particle B
First Stage Polymerization
188.2 parts of deionized water was charged in a four-necked separable flask equipped with a stiffer, a thermometer, a condenser, and a dripping funnel. 66.0 parts of the thus-obtained seed particle emulsion B was dripped thereto and thereafter, the resultant was heated to 80 degrees C. while being stirred. 2.4 parts of butyl acrylate, 1.1 parts of butylmethacrylate, 19.5 parts of methyl methacrylate, 0.7 parts of metharylic acid, 5.0 parts of alkylbenzene sodium sulfonate (Neogen SF-20, manufactured by DKS Co. Ltd.), and 55.3 parts of deionized water were emulsified by a homo disperser to prepare a pre-emulsion 1. Thereafter, the pre-emulsion 1 was charged in the dripping funnel. Next, while keeping the internal temperature of the separable flask at 80 degrees C., the thus-prepared pre-emulsion 1 was uniformly dripped in 30 minutes and at the same time, 1.2 parts of 10 percent by mass ammonium persulfate aqueous solution was uniformly dripped in three hours.

Second Stage Polymerization
254.8 parts of styrene, 5.0 parts of alkylbenzene sodium sulfonate (Neogen SF-20, manufactured by DKS Co. Ltd.), and 51.8 parts of deionized water were emulsified by a homo disperser to prepare a pre-emulsion 2. Thereafter, the pre-emulsion 2 was charged in the dripping funnel. One hour after the completion of the dripping of the pre-emulsion 1, the thus-prepared pre-emulsion 2 was uniformly dripped in 60 minutes and at the same time, 3.5 g of 10 percent by mass sodium persulfate aqueous solution were uniformly dripped in 60 minutes while keeping the internal temperature of the separable flask at 80 degrees C. After the completion of the dripping of the pre-emulsion 2, 7.5 parts of 28 percent by mass ammonium water was dripped and the system was aged at 80 degrees C. for one hour to swell and dissolve the seed particle. Subsequent to cooling down, the resultant was filtrated with a filter cloth of 120 mesh to obtain a hollow resin particle B having a concentration of solid portion of 20 percent by mass.

When the thus-obtained hollow resin particle B was subject to structure analysis using microscopic FT-IR measuring device (iN10MX/iZ10, manufactured by Thermo Fisher Scientific K.K.) and analysis software (OMNIC), the hollow resin particle B was confirmed to contain the structure unit represented by the following Chemical formula 1 and the structure unit represented by the following Chemical formula 2. The ratio (Y/X) was 3.0.

The volume average particle diameter of the thus-obtained hollow resin particle B was measured using a particle size analyzer (Nanotrac, Wave-UT151, manufactured by MicrotracBEL Corp.). The outer diameter was 700 nm and the inner diameter was 600 nm.

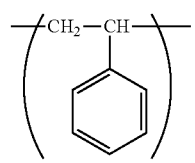

Chemical formula 1

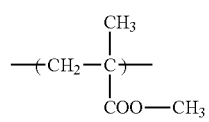

Chemical formula 2

Preparation Example 2 of Hollow Resin Particle

Preparation of Hollow Resin Particle C
A hollow resin particle C having a concentration of solid portion of 20.5 percent by mass was obtained in the same manner as in the Preparation Example 1 of the hollow resin particle except that the proportion of styrene in the second stage polymerization was changed to 39.0 percent by mass.

When the hollow resin particle C was subject to the structure analysis in the same manner as in the Preparation Example 1, the hollow resin particle C was confirmed to contain the structure unit represented by the following Chemical formula 1 and the structure unit represented by the following Chemical formula 2. The ratio (Y/X) was 4.5.

The volume average particle diameter of the thus-obtained hollow resin particle C was measured using a particle size analyzer (Nanotrac, Wave-UT151, manufactured by MicrotracBEL Corp.). The outer diameter was 800 nm and the inner diameter was 700 nm.

Preparation Example 3 of Hollow Resin Particle

Preparation of Hollow Resin Particle D
A hollow resin particle D having a concentration of solid portion of 26 percent by mass was obtained in the same manner as in the Preparation Example 1 of the hollow resin particle except that the content of styrene in the second stage polymerization was changed to 22.3 percent by mass.

When the hollow resin particle D was subject to the structure analysis in the same manner as in the Preparation Example 1, the hollow resin particle D was confirmed to contain the structure unit represented by the following Chemical formula 1 and the structure unit represented by the following Chemical formula 2. The ratio (Y/X) was 6.0.

The volume average particle diameter of the thus-obtained hollow resin particle D was measured using a particle size analyzer (Nanotrac, Wave-UT151, manufactured by MicrotracBEL Corp.). The outer diameter was 500 nm and the inner diameter was 400 nm.

Preparation Example 1 of Ink

Preparation of Ink 1

10.0 percent by mass (concentration of solid portion) of the hollow resin particle B, 25.0 percent by mass of 1,2-propane diol (manufactured by Tokyo Chemical Industry Co. Ltd.), 8.0 percent by mass of 1,2-butane diol (manufactured by Tokyo Chemical Industry Co. Ltd.), 1.0 percent by mass of surfactant (KF-640, manufactured by Shin-Etsu Chemical Co., Ltd.), 0.5 percent by mass of a defoaming agent (KF-353, manufactured by Shin-Etsu Chemical Co., Ltd.), 0.1 percent by mass of antifungus agent (LV(S), manufactured by AVECIA GROUP), a suitable amount of pH regulator (2-amino-2-ethyl-1,3-propane diol, manufactured by Tokyo Chemical Industry Co. Ltd.), and a balance of deionized water added to make the total 100 percent, were stirred and uniformly mixed for one hour to obtain a liquid mixture.

The thus-obtained liquid mixture was filtrated under a pressure with a polyvinilydene fluoride membrane filter having an average hole diameter of 5 μm (DISMIC®, 25CS080AS, manufactured by Toyo Roshi Kaisha, Ltd.) to remove coarse particles and dusts. Thus, ink 1 was obtained. pH was adjusted to be from 9 to 10. pH can be measured by a pH meter (HM-30R, manufactured by DKK-TOA CORPORATION) and the temperature of the ink 1 was set to be 25 degrees C.

Ink Preparation Examples 2 to 20

Preparation of Inks 2 to 20

Inks 2 to 20 were obtained in the same manner as in Preparation Example 1 of Ink except that the composition was changed to those shown in Tables 1 to 3. The compositions in Tables 1 to 3 were represented in the concentration of solid portion (effective component).

TABLE 1

| | | Ink | | | | | | |
|---|---|---|---|---|---|---|---|---|
| | | 1 | 2 | 3 | 4 | 5 | 6 | 7 |
| Hollow Resin | Hollow resin particle A | — | — | — | — | — | — | — |
| | Hollow resin particle B | 10.0 | — | — | — | — | — | — |
| | Hollow resin particle C | — | 10.0 | — | — | — | — | — |
| | Hollow resin particle D | — | — | 3.0 | 5.0 | 10.0 | 12.5 | 14.0 |
| | Hollow resin particle E | — | — | — | — | — | — | — |
| Organic solvent | Glycerin {SP value: 17.4 $(cal/cm^3)^{0.5}$} | — | — | — | — | — | — | — |
| | 1,2-propanediol {SP value: 14.3 $(cal/cm^3)^{0.5}$} | 25.0 | 25.0 | 30.0 | 29.0 | 25.0 | 23.0 | 22.0 |
| | 1,2-butane diol {SP value: 13.1 $(cal/cm^3)^{0.5}$} | 8.0 | 8.0 | 10.0 | 9.0 | 8.0 | 7.5 | 7.0 |
| | •3-ethyl-3-hydroxymethyl oxetane {SP value: 11.0 $(cal/cm^3)^{0.5}$} | — | — | — | — | — | — | — |
| | 3-methoxy-N,N-dimethyl propionamide {SP value: 9.2 $(cal/cm^3)^{0.5}$} | — | — | — | — | — | — | — |
| Acrylic silicone resin | Acrylic silicone resin (Tg: −7 degrees C.) | — | — | — | — | — | — | — |
| Polyurethane resin | Polyurethane resin A (Tg: −10 degrees C.) | — | — | — | — | — | — | — |
| | Polyurethane resin B (Tg: 41 degrees C.) | — | — | — | — | — | — | — |
| Other Components | Polyethylene-based wax | — | — | — | — | — | — | — |
| | Surfactant | 1.0 | 1.0 | 1.0 | 1.0 | 1.0 | 1.0 | 1.0 |
| | Defoaming agent | 0.5 | 0.5 | 0.5 | 0.5 | 0.5 | 0.5 | 0.5 |
| | Antibacterial Agent | 0.1 | 0.1 | 0.1 | 0.1 | 0.1 | 0.1 | 0.1 |
| | pH regulator | Proper quantity | Proper quantity | Proper quantity | Proper quantity | Proper quantity | Proper quantity | Proper quantity |
| | Deionized water | Balance | Balance | Balance | Balance | Balance | Balance | Balance |
| | Total (Percent by mass) | 100 | 100 | 100 | 100 | 100 | 100 | 100 |
| | Mixing SP value of organic solvent $[(cal/cm^3)^{0.5}]$ | 14.0 | 14.0 | 14.0 | 14.0 | 14.0 | 14.0 | 14.0 |

TABLE 2

| | | Ink | | | | | | |
|---|---|---|---|---|---|---|---|---|
| | | 8 | 9 | 10 | 11 | 12 | 13 | 14 |
| Hollow resin | Hollow resin particle A | — | — | — | — | — | — | — |
| | Hollow resin particle B | — | — | — | — | — | — | — |
| | Hollow resin particle C | — | — | — | — | — | — | — |
| | Hollow resin particle D | 10.0 | 10.0 | 10.0 | 10.0 | 10.0 | 10.0 | 10.0 |
| | Hollow resin particle E | — | — | — | — | — | — | — |

TABLE 2-continued

|  |  | Ink 8 | Ink 9 | Ink 10 | Ink 11 | Ink 12 | Ink 13 | Ink 14 |
|---|---|---|---|---|---|---|---|---|
| Organic solvent | Glycerin {SP value: 17.4 $(cal/cm^3)^{0.5}$} | — | — | — | — | — | — | — |
|  | 1,2-propanediol {SP value: 14.3 $(cal/cm^3)^{0.5}$} | 23.0 | 23.0 | 23.0 | 22.0 | 18.0 | 5.0 | 5.0 |
|  | 1,2-butane diol {SP value: 13.1 $(cal/cm^3)^{0.5}$} | 7.0 | 7.0 | 7.0 | 6.0 | 5.0 | — | — |
|  | •3-ethyl-3-hydroxymethyl oxetane {SP value: 11.0 $(cal/cm^3)^{0.5}$} | — | — | — | — | — | 5.0 | 15.0 |
|  | 3-methoxy-N,N-dimethyl propionamide {SP value: 9.2 $(cal/cm^3)^{0.5}$} | — | — | — | — | — | 20.0 | 10.0 |
| Acrylic silicone resin | Acrylic silicone resin (Tg: −7 degrees C.) | 1.0 | 3.0 | — | 5.0 | 10.0 | 3.0 | 3.0 |
| Polyurethane resin | Polyurethane resin A (Tg: −10 degrees C.) | — | — | 3.0 | — | — | — | — |
|  | Polyurethane resin B (Tg: 41 degrees C.) | — | — | — | — | — | — | — |
| Other Components | Polyethylene-based wax | — | — | — | — | — | — | — |
|  | Surfactant | 1.0 | 1.0 | 1.0 | 1.0 | 1.0 | 1.0 | 1.0 |
|  | Defoaming agent | 0.5 | 0.5 | 0.5 | 0.5 | 0.5 | 0.5 | 0.5 |
|  | Antibacterial Agent | 0.1 | 0.1 | 0.1 | 0.1 | 0.1 | 0.1 | 0.1 |
|  | pH regulator | Proper quantity | Proper quantity | Proper quantity | Proper quantity | Proper quantity | Proper quantity | Proper quantity |
|  | Deionized water | Balance | Balance | Balance | Balance | Balance | Balance | Balance |
|  | Total (Percent by mass) | 100 | 100 | 100 | 100 | 100 | 100 | 100 |
|  | Mixing SP value of organic solvent [$(cal/cm^3)^{0.5}$] | 14.0 | 14.0 | 14.0 | 14.0 | 14.0 | 10.4 | 11.0 |

TABLE 3

|  |  | Ink 15 | Ink 16 | Ink 17 | Ink 18 | Ink 19 | Ink 20 |
|---|---|---|---|---|---|---|---|
| Hollow Resin | Hollow resin particle A | — | — | — | — | 10.0 | — |
|  | Hollow resin particle B | — | — | — | — | — | — |
|  | Hollow resin particle C | — | — | — | — | — | — |
|  | Hollow resin particle D | 10.0 | 10.0 | 10.0 | 10.0 | — | — |
|  | Hollow resin particle E | — | — | — | — | — | 10.0 |
| Organic solvent | Glycerin {SP value: 17.4 $(cal/cm^3)^{0.5}$} | — | — | 13.0 | 18.0 | — | — |
|  | 1,2-propanediol {SP value: 14.3 $(cal/cm^3)^{0.5}$} | 22.0 | 23.0 | 20.0 | 15.0 | 25.0 | 25.0 |
|  | 1,2-butane diol {SP value: 13.1 $(cal/cm^3)^{0.5}$} | 7.0 | 7.0 | — | — | 8.0 | 8.0 |
|  | •3-ethyl-3-hydroxymethyl oxetane {SP value: 11.0 $(cal/cm^3)^{0.5}$} | — | — | — | — | — | — |
|  | 3-methoxy-N,N-dimethyl propionamide {SP value: 9.2 $(cal/cm^3)^{0.5}$} | — | — | — | — | — | — |
| Acrylic silicone resin | Acrylic silicone resin (Tg: −7 degrees C.) | 3.0 | — | — | — | — | — |
| Polyurethane resin | Polyurethane resin A (Tg: −10 degrees C.) | — | — | — | — | — | — |
|  | Polyurethane resin B (Tg: 41 degrees C.) | — | 3.0 | — | — | — | — |
| Other Components | Polyethylene-based wax | 1.0 | — | — | — | — | — |
|  | Surfactant | 1.0 | 1.0 | 1.0 | 1.0 | 1.0 | 1.0 |
|  | Defoaming agent | 0.5 | 0.5 | 0.5 | 0.5 | 0.5 | 0.5 |
|  | Antibacterial Agent | 0.1 | 0.1 | 0.1 | 0.1 | 0.1 | 0.1 |
|  | pH regulator | Proper quantity | Proper quantity | Proper quantity | Proper quantity | Proper quantity | Proper quantity |
|  | Deionized water | Balance | Balance | Balance | Balance | Balance | Balance |
|  | Total (Percent by mass) | 100 | 100 | 100 | 100 | 100 | 100 |
|  | Mixing SP value of organic solvent [$(cal/cm^3)^{0.5}$] | 14.0 | 14.0 | 15.5 | 16.0 | 14.0 | 14.0 |

In Tables 1 to 3, the product names and the manufacturing companies of the ingredients are as follows:

Hollow resin particle A: copolymer of styrene and methylmethacrylate, ROPAQUR ULTRA E, ratio (Y/X): 1.5, outer diameter: 500 nm, inner diameter: 400 nm, concentration of solid portion: 30 percent by mass, manufactured by The Dow Chemical Company Hollow resin particle E: copolymer of styrene and methylmethacrylate, SX868, ratio (Y/X): 9.3, outer diameter: 700 nm, inner diameter: 500 nm, concentration of solid portion: 20.3 percent by mass, manufactured by JSR Corporation Glycerin: SP Value: 17.4 $(cal/cm^3)^{0.5}$, manufactured by Sakamoto Yakuhin kogyo Co., Ltd.

1,2-propane diol: SP Value: 14.3 $(cal/cm^3)^{0.5}$, manufactured by Tokyo Chemical Industry Co. Ltd.

1,2-butane diol: SP Value: 13.1 $(cal/cm^3)^{0.5}$, manufactured by Tokyo Chemical Industry Co. Ltd.

3-ethyl-3-hydroxydimethyl oxetane: SP Value: 11.0 $(cal/cm^3)^{0.5}$, manufactured by Tokyo Chemical Industry Co. Ltd.

3-methoxy-N,N-dimethylpropioneamide: SP value: 9.2 $(cal/cm^3)^{0.5}$, manufactured by Idemitsu Kosan Co., Ltd.

Acrylic silicone-based resin: RKP-02, Tg: −7 degrees C., manufactured by TOYOCHEM CO., LTD.

Polyurethane resin A, SUPERFLEX® 420, Tg: −10 degrees C., concentration of solid portion: 38 percent by mass, manufactured by DKS Co. Ltd.

Polyurethane resin B, SUPERFLEX® 210, Tg: 41 degrees C., Concentration of solid portion: 35 percent by mass, manufactured by DKS Co. Ltd.

Polyethylene wax, AQUACER-515, manufactured by BYK

Surfactant: KF-640, manufactured by Shin-Etsu Chemical Co., Ltd.

Defoaming agent: KF-353, manufactured by Shin-Etsu Chemical Co., Ltd.

Antifungus Agent: LV(S), manufactured by AVECIA GROUP pH regulator: 2-amino-2-ethyl-1,3-propane diol, manufactured by Tokyo Chemical Industry Co. Ltd.

Sedimentation property of the obtained ink was evaluated in the following manner. The results are shown in Table 4.

Sedimentation

About 5 g of the obtained ink was placed in a glass tube (screw-top test tube, manufactured by AS ONE Corporation.) and left still at 25 degrees C. for 168 hours. A sample of 0 hours (initial value) and a sample stored for 168 hours were measured by a sedimentation measuring device (Turbiscan MA2000, manufactured by EKO Instruments) to calculate the sedimentation ratio. A small sedimentation ratio reads great sedimentation. Sedimentation ratio of −2.0 percent or greater is practically allowable.

Examples 1 to 18 and Comparative Examples 1 and 2

Images were formed on a recording medium using the obtained ink in the following manner to obtain recorded matter.

The cross-section of the obtained recorded matter was observed by a microscope (JSM-6510, manufactured by JEOL Ltd.) and the diameter of 10 voids (hollows) selected at random was measured. The diameter of the voids in the image of the obtained recorded matter was obtained based on the average of the measuring result. If the hollow was not a true circle, the maximum of the diameter was used to calculate the average diameter.

The void (diameter) in the image of the obtained recorded matter is as follows.

Recorded matter including the hollow resin particle A: 400 nm

Recorded matter including the hollow resin particle B: 600 nm

Recorded matter including the hollow resin particle C: 700 nm

Recorded matter including the hollow resin particle D: 400 nm

Recorded matter including the hollow resin particle E: 500 nm

Image Forming

The obtained ink was discharged onto a recording medium (Luminacolorblack, 127 gsm, manufactured by TAKEO Co., Ltd.) with an attached amount of 600 $mg/cm^2$ by a liquid discharging device (IPSiO GXe550, manufactured by Ricoh Company Ltd.). Thereafter, the recording medium was dried at 90 degrees C. for 60 seconds using a constant temperature tank (FX420P, manufactured by Kusumoto Chemicals, Ltd.) to obtain an initial sample (recorded matter) The print chart was a square image of 3 cm×3 cm formed with dot patterns.

Measuring of Absorbance of Image

The absorbance (X) of the thus-obtained initial sample at the maximum absorption wavelength in a range of from 1,590 to 1,610 $cm^{-1}$ and the absorbance (Y) of the thus-obtained initial sample at the maximum absorption wavelength in a range of from 1,720 to 1,740 $cm^{-1}$ using IR spectrum with microscopic FT-IR measuring device (iN10MX/iZ10, manufactured by Thermo Fisher Scientific K.K.) and analysis software (OMNIC). The ratio (Y/X) was calculated based on the values of the obtained absorbance (X) and the absorbance (Y). The results are shown in Table 4.

Fixability of the obtained recorded matter was evaluated in the following manner. The results are shown in Table 4.

Fixability

The thus-obtained initial sample was abraded back and forth five times by a clock meter (manufactured by DAIEI KAGAKU SEIKI MFG. co., ltd.) to which a cotton cloth was attached. The image density before and after the abrasion was measured using a spectrophotometer (939, manufactured by X-Rite). Fixability was calculated from the difference of density between before and after the abrasion to evaluation fixability.

Luminosity (L*)

Luminosity (L*) of the initial sample obtained from the image forming was measured using a spectrophotometer (939, X-Rite). Next, using a constant temperature tank (FX420P, manufactured by Kusumoto Chemicals, Ltd.), the initial sample was dried at 110 degrees C. for 60 seconds to obtain a secondary sample. Luminosity (L*) of the thus-obtained secondary sample was measured in the same manner as for the initial sample. Based on the luminosity (L*) of the obtained initial sample and secondary sample (value after being dried at 100 degrees C. for 60 seconds), the change ratio (percent) of luminosity (L*) was calculated. The results are shown in Table 4.

The change ratio (percent)={(initial value−value obtained after heated at 110 degrees C. for 60 seconds)/initial value}100     Relation 1

TABLE 4

|  |  |  |  | Proportion (percent by mass) of resin to image | | |
| --- | --- | --- | --- | --- | --- | --- |
|  |  | Ink No, | Ratio (Y/X) | Hollow Resin | Acrylic silicone resin | Polyurethane resin |
| Example | 1 | 1 | 3.0 | 100.0 | 0.0 | 0.0 |
|  | 2 | 2 | 4.5 | 100.0 | 0.0 | 0.0 |
|  | 3 | 3 | 6.0 | 100.0 | 0.0 | 0.0 |
|  | 4 | 4 | 6.0 | 100.0 | 0.0 | 0.0 |
|  | 5 | 5 | 6.0 | 100.0 | 0.0 | 0.0 |
|  | 6 | 6 | 6.0 | 100.0 | 0.0 | 0.0 |

TABLE 4-continued

|  |  |  |  |  |  |  |
|---|---|---|---|---|---|---|
|  | 7 | 7 | 6.0 | 100.0 | 0.0 | 0.0 |
|  | 8 | 8 | 6.0 | 90.9 | 9.1 | 0.0 |
|  | 9 | 9 | 6.0 | 76.9 | 23.1 | 0.0 |
|  | 10 | 10 | 6.0 | 76.9 | 0.0 | 23.1 |
|  | 11 | 11 | 6.0 | 66.7 | 33.3 | 0.0 |
|  | 12 | 12 | 6.0 | 50.0 | 50.0 | 0.0 |
|  | 13 | 13 | 6.0 | 76.9 | 23.1 | 0.0 |
|  | 14 | 14 | 6.0 | 76.9 | 23.1 | 0.0 |
|  | 15 | 15 | 6.0 | 76.9 | 23.1 | 0.0 |
|  | 16 | 16 | 6.0 | 76.9 | 0.0 | 23.1 |
|  | 17 | 17 | 6.0 | 100.0 | 0.0 | 0.0 |
|  | 18 | 18 | 6.0 | 100.0 | 0.0 | 0.0 |
| Comparative Example | 1 | 19 | 1.5 | 100.0 | 0.0 | 0.0 |
|  | 2 | 20 | 9.3 | 100.0 | 0.0 | 0.0 |

Evaluation Results

|  |  | Luminosity | | Change ratio (percent) | Sedimentation (percent) | Fixability (percent) |
|---|---|---|---|---|---|---|
|  |  | Initial sample | Secondary sample (heated at 110 degrees C.) | | | |
| Example | 1 | 64 | 53 | 17.0 | −0.8 | 79 |
|  | 2 | 60 | 51 | 15.0 | −0.8 | 83 |
|  | 3 | 48 | 41 | 15.0 | −0.3 | 89 |
|  | 4 | 53 | 46 | 14.0 | −0.5 | 87 |
|  | 5 | 56 | 49 | 12.0 | −0.9 | 85 |
|  | 6 | 67 | 55 | 18.0 | −1.2 | 85 |
|  | 7 | 69 | 56 | 19.0 | −1.5 | 83 |
|  | 8 | 60 | 52 | 13.3 | −1.2 | 86 |
|  | 9 | 62 | 55 | 11.0 | −1.2 | 90 |
|  | 10 | 58 | 50 | 13.0 | −1.2 | 94 |
|  | 11 | 64 | 57 | 11.0 | −1.2 | 96 |
|  | 12 | 55 | 48 | 12.7 | −1.2 | 95 |
|  | 13 | 45 | 34 | 24.0 | −1.2 | 95 |
|  | 14 | 55 | 43 | 21.0 | −1.0 | 97 |
|  | 15 | 63 | 56 | 11.1 | −1.2 | 95 |
|  | 16 | 58 | 45 | 22.4 | −1.2 | 84 |
|  | 17 | 59 | 54 | 8.0 | −1.2 | 80 |
|  | 18 | 62 | 57 | 8.0 | −1.3 | 76 |
| Comparative Example | 1 | 68 | 50 | 26.0 | −0.5 | 70 |
|  | 2 | 38 | 35 | 9.0 | −2.5 | 97 |

Aspects of the present disclosure are, for example, as follows.

1. A recorded matter includes a recording medium and an image on the recording medium. The image contains a hollow resin including a copolymer of the structure unit represented by the following chemical formula 1 and the structure unit represented by the following chemical formula 2. The image satisfies the following ratio: $3.0 \leq Y/X \leq 6.0$, where X represents the absorbance of the image at the maximum absorption wavelength in a range of from 1,590 to 1,610 cm$^{-1}$ and Y represents the absorbance of the image at the maximum absorption wavelength in a range of from 1,720 to 1,740 cm$^{-1}$.

Chemical formula 1

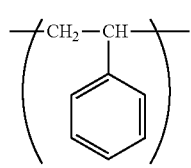

Chemical formula 2

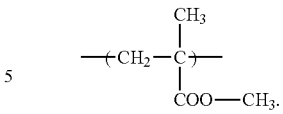

2. The recorded matter according to 1 mentioned above, wherein the hollow resin accounts for 50 to 100 percent by mass of the total mass of the image.

3. The recorded matter according to 1 or 2 mentioned above, wherein the image is formed using an ink containing a hollow resin particle accounting for 5.0 to 12.5 percent by mass of the total mass of the ink.

4. The recorded matter according to any one of 1 to 3 mentioned above, wherein the image further contains an acrylic silicone resin and a polyurethane resin.

5. The recorded matter according to 4 mentioned above, wherein the acrylic silicone resin accounts for 21.4 to 33.3 percent by mass and the polyurethane resin accounts for 21.4 to 33.3 percent by mass.

6. The recorded matter according to 4 or 5 mentioned above, wherein the image is formed using an ink containing a hollow resin particle accounting for 5.0 to 12.5 percent by mass of the total mass of the ink and the acrylic silicone resin accounts for 3 to 5 percent by mass of the total mass of the ink and the polyurethane resin accounts for 3 to 5 percent by mass of the total mass of the ink.

7. The recorded matter according to any one of 4 to 6 mentioned above, wherein the acrylic silicone resin has a glass transition temperature of 0 degrees C. or lower and the polyurethane resin has a glass transition temperature of 0 degrees C. or lower.

8. The recorded matter according to any one of 1 to 7 mentioned above, wherein the image further contains an organic solvent and the mixing SP value of the organic solvent is from 11.0 to 15.5 $(cal/cm^3)^{0.5}$.

9. The ink according to any one of 1 to 8 mentioned above, wherein the volume average particle diameter of the hollow resin is from 400 to 800 nm.

10. The recorded matter according to 8 or 9 mentioned above, wherein the hydrogen bond terms of Hansen solubility parameter (HSP) of the organic solvent is from 3 to 6.8 $(cal/cm^3)^{0.5}$.

11. The recorded matter according to any one of 8 to 10 mentioned above, wherein the organic solvent is at least one member selected from the group consisting of 1,2-propane diol, 1,3-propane diol, 1,2-butane diol, 1,3-butane diol, isoprene glycol, and an oxetane compound.

12. The recorded matter according to claim 11 mentioned above, wherein the oxetane compound includes 3-ethyl-3-hydroxymethyl oxetane.

13. The recorded matter according to any one of 8 to 12 mentioned above, wherein the proportion of the organic solvent accounts for 10 to 60 percent by mass of the total mass of the image.

14. The recorded matter according to any one of 1 to 13 mentioned above, wherein the image further contains wax.

15. The recorded matter according to 14 mentioned above, wherein the wax includes at least one of polyethylene wax and carnauba wax.

16. The ink according to 14 or 15 mentioned above, wherein the wax has a melting point of from 80 to 140 degrees C.

17. The recorded matter according to any one of 14 to 16 mentioned above, wherein the volume average particle diameter of the wax is from 0.01 µm or greater.

18. The recorded matter according to any one of 14 to 17 mentioned above, wherein the proportion of the wax accounts for 1 to 10 percent by mass of the total mass of the image.

19. The recorded matter according to any one of 1 to 18 mentioned above, wherein the image further contains a surfactant.

20. The recorded matter according to 19 mentioned above, wherein the surfactant accounts for 0.001 to 5 percent by mass of the total mass of the image.

21. The recorded matter according to any one of 1 to 20 mentioned above, wherein luminosity of the image changes 25 percent or less before and after the image is heated at 110 degrees C. for 60 seconds.

22. An ink includes a hollow resin particle containing a copolymer of the structure unit represented by the following chemical formula 1 and the structure unit represented by the following chemical formula 2, an organic solvent, and water. In an IR spectrum of the hollow resin particle, the hollow resin particle satisfies the following ratio: $3.0 \leq Y/X \leq 6.0$, where X represents the absorbance of the hollow resin particle at the maximum absorption wavelength in a range of from 1,590 to 1,610 cm$^{-1}$ and Y represents the absorbance of the hollow resin particle at the maximum absorption wavelength in a range of from 1,720 to 1,740 cm$^{-1}$. The ink is used for manufacturing the recorded matter of any one of 1 to 21 mentioned above.

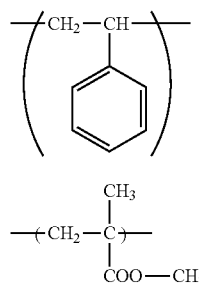

Chemical formula 1

Chemical Formula 2

23. The ink according to 22 mentioned above, wherein the organic solvent has a mixture SP value of from 10.4 to 16.0 (cal/cm$^3$)$^{0.5}$.

According to the present disclosure, a recorded matter is provided which has an image with good fixability while crushing (decrease of luminosity L*) of a hollow resin is suppressed.

Having now fully described embodiments of the present invention, it will be apparent to one of ordinary skill in the art that many changes and modifications can be made thereto without departing from the spirit and scope of embodiments of the invention as set forth herein.

What is claimed is:

1. Recorded matter comprising:
a recording medium; and
an image on the recording medium,
wherein the image comprises a hollow resin comprising a copolymer of a structure unit represented by the following chemical formula 1 and a structure unit represented by the following chemical formula 2 and
wherein, in an infrared spectroscopy (IR) spectrum of the image, the image satisfies the following ratio: $3.0 \leq Y/X \leq 6.0$, where X represents an absorbance of the image at a maximum absorption wavelength in a range of from 1,590 to 1,610 cm$^{-1}$ and Y represents an absorbance of the image at a maximum absorption wavelength in a range of from 1,720 to 1,740 cm$^{-1}$,

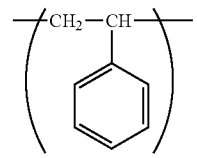

Chemical formula 1

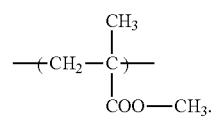

Chemical formula 2

2. The recorded matter according to claim 1, wherein the hollow resin accounts for 50 to 100 percent by mass of a total mass of the image.

3. The recorded matter according to claim 1, wherein the image is formed using an ink comprising a hollow resin particle accounting for 5.0 to 12.5 percent by mass of a total mass of the ink.

4. The recorded matter according to claim 1, wherein the image further comprises an acrylic silicone resin and a polyurethane resin.

5. The recorded matter according to claim 4, wherein the acrylic silicone resin accounts for 21.4 to 33.3 percent by mass of a total mass of the image and the polyurethane resin accounts for 21.4 to 33.3 percent by mass of the total mass of the image.

6. The recorded matter according to claim 4, wherein the image is formed using an ink comprising a hollow resin particle accounting for 5.0 to 12.5 percent by mass of a total mass of the ink and wherein the acrylic silicone resin accounts for 3 to 5 percent by mass of a total mass of the ink and the polyurethane resin accounts for 3 to 5 percent by mass of the total mass of the ink.

7. The recorded matter according to claim 4, wherein the acrylic silicone resin has a glass transition temperature of 0 degrees C. or lower and the polyurethane resin has a glass transition temperature of 0 degrees C. or lower.

8. The recorded matter according to claim 1, wherein luminosity of the image changes 25 percent or less before and after the image is heated at 110 degrees C. for 60 seconds.

9. An ink comprising:
a hollow resin particle comprising a copolymer of a structure unit represented by the following chemical formula 1 and a structure unit represented by the following chemical formula 2;
an organic solvent; and
water,
wherein, in an infrared spectroscopy (IR) spectrum of the hollow resin particle, the hollow resin particle satisfies the following ratio: $3.0 \leq Y/X \leq 6.0$, where X represents an absorbance of the hollow resin particle of a maximum absorption wavelength in a range of from 1,590 to 1,610 cm$^{-1}$ and Y represents an absorbance of the hollow resin particle of a maximum absorption wavelength in a range of from 1,720 to 1,740 cm$^{-1}$, Chemical formula 1
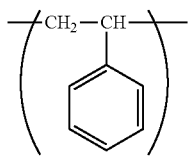
Chemical formula 2
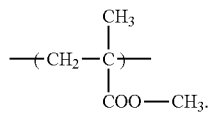
10. The ink according to claim 9, wherein the organic solvent has a mixture solubility parameter (SP) value of from 10.4 to 16.0 $(cal/cm^3)^{0.5}$.
* * * * *